United States Patent [19]

Brauer et al.

[11] 4,362,510

[45] Dec. 7, 1982

[54] CEMENTITIOUS DENTAL COMPOSITIONS WHICH DO NOT INHIBIT POLYMERIZATION

[75] Inventors: Gerhard M. Brauer, Bethesda; Harold Argentar, Rockville; Jeffrey W. Stansbury, College Park, all of Md.

[73] Assignee: The United States of America as represented by the Secretary of the Department of Health and Human Services, Washington, D.C.

[21] Appl. No.: 329,590

[22] Filed: Dec. 10, 1981

[51] Int. Cl.$^3$ ............................................. A61K 6/08
[52] U.S. Cl. ................................... 433/199; 106/35; 106/241; 260/998.11; 433/201; 433/202; 433/217; 433/228; 523/116; 524/291
[58] Field of Search .............. 433/201, 202, 199, 228; 523/115, 116, 117, 120; 260/998.11; 106/35, 241; 524/291

[56] References Cited

U.S. PATENT DOCUMENTS

| | | | |
|---|---|---|---|
| 2,936,242 | 5/1960 | Brauer | 106/35 |
| 3,509,089 | 4/1970 | Dougherty | 106/35 |
| 3,516,960 | 6/1970 | Martins et al. | 524/291 |
| 3,635,889 | 1/1972 | Bowen | 260/47 U |
| 3,804,794 | 4/1974 | Schmitt et al. | 260/29.6 M |
| 4,240,832 | 12/1980 | Jandourek | 106/35 |
| 4,280,842 | 7/1981 | Dewhirst | 106/35 |

OTHER PUBLICATIONS

Gerhard M. Brauer, "The Present State and Future of Macromolecules for Dental Applications", *Polym.--plast. Technol. Eng.*, 9, 87-121, (1977).

Gerhard M. Brauer, "A Review of Zinc Oxide--Eugenol Type Filling Materials and Cements", *Rev. Belge Med. Dent.—Belg. Tijds. vr Tandheelk.*, 20, 323-364 (1965).

Gerhard M. Brauer, "New Developments in Zinc Oxide-Eugenol Cement", *Annals of Dentistry*, 26, 44-50 (1967).

Primary Examiner—Lorenzo B. Hayes
Attorney, Agent, or Firm—Holman & Stern

[57] ABSTRACT

Cementitious dental compositions suitable for use as luting agents, sedative and insulating bases, temporary and long term restoratives, endodontic sealants, pulp capping materials, tissue packs, impression pastes and adhesives for dental composites and hard tissues comprising a solid phase which includes a metal oxide or hydroxide of tin or a Group II metal and a liquid phase which includes a chelating compound, the chelating compound being an ester of a vanillic acid moiety in which the ester is the product of a reaction of one of an alcohol, a polyhydric alcohol or a polyalkylene glycol and at least one of either vanillic acid or its isomers or homoloynes. The compositions may additionally contain a second chelating compound, Al$_2$O$_3$, an hydrogenated rosin, polymeric materials and polymerizable monomeric materials.

46 Claims, 1 Drawing Figure

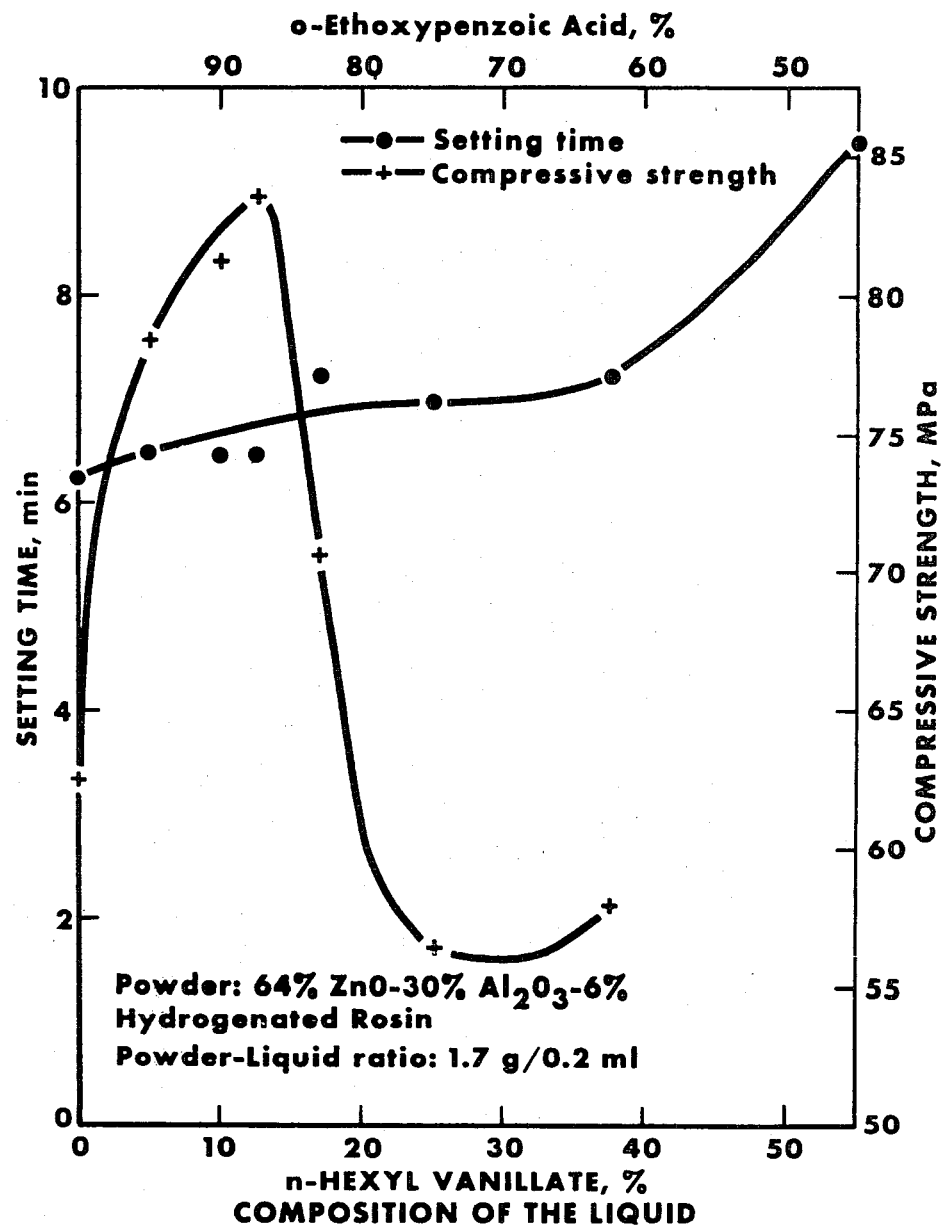

CEMENTITIOUS DENTAL COMPOSITIONS WHICH DO NOT INHIBIT POLYMERIZATION

BACKGROUND OF THE INVENTION

1. Field of the Invention

The invention relates to cementitious materials suitable for use as luting agents, sedative and insulating bases, temporary and long term restoratives, endodontic sealants, pulp capping materials, tissue packs, impression pastes and adhesives for dental composites and hard tissues. Specifically, the present invention relates to high strength, low solubility adhesives and restoratives containing vanillic acid esters and metal oxides which do not inhibit polymerization.

2. Description of the Prior Art

Oil of cloves has been used in the treatment of dental caries since the XVI century and its inclusion in combination with zinc oxide in dental cements, commonly referred to as luting agents, was reported over 100 years ago. Analysis revealed that oil of cloves contains approximately 85% by weight of eugenol. It is this latter compound which is used in zinc oxide-eugenol (hereinafter referred to as ZOE) dental cements. ZOE compositions have found wide application in dentistry including temporary restoratives, sedative bases, cementing media for crown and bridge work, in pulp capping, soft tissue packs in oral surgery and periodontics, root canal sealers in endodontics and with modifying agents as impression pastes.

ZOE cements possess much better biocompatibility than most other dental materials. They have excellent sealing characteristics and their bacteriocidal effectiveness has been well demonstrated. The cement acts as a palliative or anodyne and as a mild non-irritant antiseptic. Unfortunately, these materials have low strength, which may not be large enough to resist forces of mastication. Their lack of resistance to wear and disintegration, partially because of their high relative solubility in oral fluids of the mouth, further deters their more extensive use as temporary restorations or fillings. These materials also inhibit free radical polymerization because of the presence of an electron-rich phenolic hydroxyl group in the eugenol molecule. Thus, acrylic resins, and to a lesser extent composites, in contact with a ZOE cement do not polymerize completely. This incomplete cure results in polymer surface regions having poor physical properties such as low surface hardness. Furthermore, ZOE cements adhere only weakly to acrylic restorations, bone or dental tissues.

Although the eugenol ingredient is relatively non-toxic ($LD_{50}$ of 0.5 g/kg for white mice), free eugenol has some inflammatory characteristics. Thus, when injected into the abdominal integument and eyes of rabbits, eugenol produces severe inflammation. It produces leucocytic infiltration and polymorphonuclear responses, and in direct contact with the pulp or periodontal tissues eugenol can act as a coagulent. In in vitro tests it shows a hemolyzing, protein precipitating action.

A further disadvantage is that eugenol has a penetrating long-lasting odor and lingering taste which can be unpleasant to many patients. In addition, incompletely hardened cements containing much residual eugenol can produce irritation and toxic cell reactions.

To overcome some of these deficiencies, especially to improve the mechanical strength of the ZOE cement, research has been directed to either replacing eugenol altogether with a more suitable substitute or towards including additives in the ZOE compositions which resolve many of the problems. However, the use of eugenol substitutes has usually resulted in cements possessing poor physical properties.

Zinc oxide will react with many chelate forming compounds, especially those containing o-methoxyphenol (guaiacol) groups to yield cementitious products. Cements obtained from o-ethoxybenzoic acid (referred to hereinafter as EBA) and zinc oxide have found a considerable number of applications in dentistry because of their strength and excellent biocompatibility, especially as luting agents and as bases. However, the materials still disintegrate too rapidly under clinical conditions to be employed for more permanent restorations.

SUMMARY OF THE INVENTION

The present invention relates to high-strength cementitious dental compositions which contain no eugenol. The instant invention relates specifically to metal oxide-chelate compositions containing one or more chelating compounds, at least one of which is an ester of vanillic acid or its isomers which, because of the absence of eugenol or like materials, do not inhibit polymerization of monomeric materials commonly used in an oral environment, such as acrylates and methacrylates.

The compositions may contain other additives such as a rosin, a second metal oxide, polymeric materials and one or more acidic materials to impart various desirable properties to the composition both before and after curing. The cementitious materials herein described, when cured, adhere strongly to non-precious metals, amalgams, acrylic resins and composites even after prolonged exposure of the adhesive joint or interface to an aqueous environment.

The present invention also contemplates the inclusion of cross-linking agents which thereby provide compositions suitable for use as dental restoration or filling materials. Such materials include di-and polyvanillate esters and monomers which generally polymerize by a free radical mechanism.

DESCRIPTION OF THE PREFERRED EMBODIMENTS

The present invention is directed to cementitious dental compositions which provide ease of manipulation and handling in a variety of dental applications. When set, these materials are compatible with, and will not inhibit curing of, polymerizable materials of the type generally used in an oral environment, such as the acrylates and methacrylates. The compositions, when cured, provide high strength, low solubility in an oral environment, high biocompatibility and high adhesion to both acrylic and metal surfaces.

The desired ease of manipulation and handling as well as the required properties of the cured material are obtained by mixing, immediately before use, a solid phase containing one or more metal oxides in powder form with a liquid phase containing one or more chelating agents.

Metal oxides which are suitable for use in the present invention are the oxides of metals found in Groups IIA and IIB of the periodic table as well as tin oxide (Group IVB). Metal oxides as used herein would also include the hydroxides of these same metals. The oxides and hydroxides of zinc, calcium, tin, barium and magnesium are preferred and zinc oxide is the most preferred of the metal oxides.

The compounds of the present invention which form the desired chelates with the metal oxides include esters of vanillic acid (4-hydroxy -3-methoxybenzoic acid) or its isomers, as for example isovanillic acid (3-hydroxy-4-methoxybenzoic acid) or o-vanillic acid (2-hydroxy-3-methoxybenzoid acid), or homologs as for example homovanillic acid which are liquids at or within 30° C. above room temperature. The esters of the latter compound in high concentration may be somewhat inhibiting. Vanillic acid, itself a solid, may be used in the present invention, however, with the exception set forth below, is generally unsuitable since it is a solid at room temperature and most solvents which may be used to effect solution are undesirable because of toxic properties or the manner in which they influence curing or the final cured composition.

The esters of vanillic acid and its isomers suitable for use in the present invention include those compounds in which the alcoholic radical results in the ester being a liquid at a temperature of approximately 55° C. Such groups include saturated, unsaturated, branched and straight chain alkyl groups. Arylalkyl groups are also suitable when they result in a liquid ester at or within 30° C. of room temperature. The present invention also includes di-and polyvanillate esters of polyfunctional radicals, such as may be derived from glycols and polyhydric compounds. The preferred alkyl vanillates are those having a straight or branched chain alkyl group having between 4 and 15 carbon atoms. When the alkyl group is a straight chain radical, between 5 and 12 carbon atoms is preferred, with hexyl vanillate being most preferred. Replacing hexyl vanillate with other esters of vanillic acid yield cements with properties similar to those employing hexyl vanillate. However, these cements may possess specific properties such as increased hydrophobicity which makes the hardened material more desirable for specific applications in dentistry where water repellancy and minimum solubility of the material in the mouth's fluids is of prime importance.

As indicated above, isomers of vanillic acid may be used when they result in an ester which is a liquid at or within 30° C. of ambient temperature. The preferred isomers are those having the methoxy and hydroxy groups in adjacent or ortho positions to each other. The most preferred isomers are o-vanillic and isovanillic esters. Homologs of vanillic acid and its isomers are also suitable, as for example homovanillic acid or the acids in which an ethoxy group has been substituted for a methoxy group.

The alkyl vanillates of the present invention may be prepared by conventional techniques such as by refluxing vanillic acid, or one of its isomers, with the corresponding alcohol in the presence of a catalytic amount of a suitable acid such as p-toluensulfonic acid. After a reflux period suitable to accomplish extensive conversion to the ester, unreacted alcohol is removed by distillation under vacuum. Specific details of an acceptable procedure are given in I. A. Pearl, et al., "Reaction of Vanillin and Its Derived Compounds. Some Esters of Vanillic Acid", JOURNAL OF THE AMERICAN CHEMICAL SOCIETY, volume 69, p. 3071 (1947).

Although the basic two component metal oxide-vanillate ester system of the present invention, preferably zinc oxide-hexyl vanillate (hereinafter referred to as ZO-HV), provides the advantages over similar cementitious compositions which are enumerated above, additional improvements may be realized by inclusion of other components in the basic powder-liquid system. For instance, when an ester such as hexyl vanillate is mixed with zinc oxide, having a preferred particle size corresponding to a #70 sieve or smaller, a cohesive cement is formed slowly, approaching its fully hardened state only after several hours. By including a second liquid chelating compound with the vanillate ester in the liquid phase, the former appears to provide an additional solvent effect, but more importantly, hardening is accelerated. Suitable solvent-chelating agents include those compounds which are liquid and contain groups capable of chelating or reacting with the metal oxide like the vanillate esters, forming a ring in which the metal ion is at the center of a coordination complex. These compounds must also be able to dissolve the vanillate ester. Appropriate solvent-chelating compounds should also lack polymerization inhibiting groups. Preferred compounds would include o-ethoxybenzoic acid (referred to hereinafter as EBA), ethoxyacetic acid, lactic acid, salicylaldehyde, 2-propoxy-5-methylbenzoic acid and, if non-inhibition of polymerization is less important than strength, alkoxyphenols, generally. The preferred compound is EBA which has demonstrated efficacy in similar cementitious compositions for certain types of dental applications. Vanillic acid itself is slightly soluble in EBA, thus providing a means for using the non-esterified compound. However, the low solubility limits the utility of zinc oxide-vanillic acid-EBA systems. Typical results obtained with mixes containing solutions of these chelating agents with the preferred powder composition of 64% zinc oxide, 30% aluminum oxide, 6% hydrogenated rosin powder and a powder/liquid (P/L) ratio of 1.7 g/0.2 ml are given in Table 1 and the figure. Suitable results are obtained with liquids containing 2.5 to 35% vanillate and 65 to 97.5% of a second chelator. The optimum physical properties are obtained, however, with liquids containing 5 to 25% vanillate ester, by weight and 75 to 95% of an additional chelating compound. The cement containing 12.5% hexyl vanillate hardened in 6.5 min to provide the highest compressive and tensile strength.

TABLE 1

Properties of Hexyl Vanillate-o-Ethoxybenzoic Acid Cements with Zinc Oxide-Aluminum Oxide-Hydrogenated Rosin Powders

| Composition of Liquid | | | Properties of Cement[a] | |
| --- | --- | --- | --- | --- |
| n-Hexyl Vanillate (%) | EBA (%) | Setting Time (min.) | Strength | |
| | | | Compressive (MPa) | Tensile (MPa) |
| 100 | — | >180 | — | — |
| 50 | 50 | 9.5 | — | — |
| 37.5 | 62.5 | 7.25 | 57.9 ± 12.7 | — |
| 25 | 75 | 7.0 | 56.4 ± 10.6 | — |
| 17 | 83 | 7.25 | 70.6 ± 10.6 | 5.6 ± 0.3 |
| 12.5 | 87.5 | 6.5 | 83.6 ± 11.0 | 6.2 ± 0.8 |
| 10 | 90 | 6.5 | 81.3 ± 12.1 | — |
| 5 | 95 | 6.5 | 78.4 ± 5.4 | 6.0 ± 1.1 |
| 0 | 100 | 6.25 | 62.6 ± 9.0 | — |

[a]Powder-liquid ratio: 1.7 g/0.2 ml
Powder: 64% ZnO - 30% Al$_2$O$_3$ - 6% Hydrogenated Rosin Further reductions in setting time may be achieved by addition of small amounts of acid to the liquid phase prior to mixing. Although a mineral acid may be employed, organic acids, particularly carboxylic acids, prove quite effective. Preferred acids would include acetic acid, acrylic acid, methacrylic acid, polyacrylic acid, benzoic acid, hydrocinnamic acid and polycarboxylated polystyrene. A substance which is both a carboxylic acid and capable of forming a chelate with a metal oxide is frequently preferred, depending upon other variables related to the interactions with other components and their concentrations in the mixture as well as the ultimate application of the cementitious material. Many of the compounds indicated above as preferred chelating compounds serve both purposes. In addition, dimethylolpropionic acid has proven quite effective in this dual capacity.

A comparison of the effect on setting time of added acid with a typical ZO-HV-EBA composition according to the present invention is given in Table 2. The amount of acid present should preferably be in the range of 0.05–15%, based on the weight of liquid phase and most preferably be between 0.1 and 10%.

TABLE 2

Effect of Acid Addition on the Properties of ZO-HV-EBA Cements

Composition: Powder: 64% ZnO; 30% $Al_2O_3$; 6% Hydrogenated Rosin
Liquid: 12.5% Hexyl Vanillate; 87.5% EBA
Powder/Liquid Ratio: 1.3 g/0.2 ml

| Acid Added to Liquid (% of liquid phase) | Setting Time (min) | Strength Compressive (MPa) | Tensile (MPa) |
|---|---|---|---|
| — | 6.5 | 83.6 ± 11.0 | 6.2 ± 0.8 |
| 0.1 Acetic | 5.5 | 61.4 ± 11.2 | 5.0 ± 0.1 |
| 0.1 Acetic | 4.5 | 55.1 ± 17.5 | — |
| 1 Acetic | 2–2.5 | — | — |
| 0.1 Acrylic | 5 | 54.3 ± 14.5 | — |
| 1 Acrylic | 3 | 40.3 ± 6.4 | — |
| 10 Acrylic | 0.3 | — | — |
| 1 Benzoic | 5.0 | — | — |
| 1 Polyacrylic (MW = 20,000) | 4 | — | — |
| 1 Polycarboxylated Polystyrene | 4.5 | — | — |
| 0.8 Dimethylolpropionic | 4 | 71.7 ± 7.1 | 6.4 ± 0.8 |
| 1 Hydrocinnamic | 6 | — | — |

The compressive strength measured one day after setting of the composition listed in Table 2 which has added acid other than the chelating compound, EBA, is 83.6 MPa. The diametral tensile strength is 6.2 MPa. This compares most favorably with ZOE cements which, measured one week after setting, and compressive strengths in the range of 16–38 MPa and tensile strengths in the range of 1.4–2.5 MPa.

As noted in the heading of Table 2, a preferred composition may contain several other components in the powder phase. A reinforcing agent of the type commonly used in such compositions may be added to improve compressive strength and lower film thickness. Fused quartz, glass, silica and aluminum oxide are examples of suitable reinforcing agents with $Al_2O_3$ having particle sizes between $0.5\mu$ to $20\mu$ being preferred. The concentration of the latter being preferably in the range of 0–50%, based on the weight of the solid phase, and most preferably 30% by weight.

Rosin, rosin esters or abietic acid (the major constituent) of rosin may be added to improve consistency such as lower film thicknesses and smoother mixing characteristics. Unfortunately, these materials also increase solubility and decrease the strength of the cured composition. Hydrogenated rosin, of the type sold under the same of STAYBELITE (trademark of Hercules, Inc., Wilmington, Del.), not only improves mixing characteristics but also reduces solubility and disintegration. Compressive strength varies inversely with the amount of hydrogenated resin added, but at low concentrations (below 2%) with fine ZnO particles, tends to increase the compressive strength beyond that which would occur in its absence. Hydrogenated rosin also is stable to oxidation and yields cements with good color stability. In determining the appropriate quantitative composition, the properties of ease of manipulation, curing time, hardness, solubility, adhesion and strength must be carefully considered since variation both in type and amounts may influence more than one of these properties. However, the preferred amount of hydrogenated rosin which achieves the optimum balance of these properties is in the range of 1.5 to 15% by weight of the solid phase; 6% by weight being the most preferred concentration.

Although the preferred powder or solid phase of the present invention comprises, by weight, 40 to 98.5% ZnO, 0 to 50% $Al_2O_3$ and 1.5 to 15% hydrogenated rosin and the composition which is most preferred is 64% ZnO, 30% $Al_2O_3$ and 6% hydrogenated rosin, other substances may be substituted in part for the constituents.

Because of the electron poor nature of the hydroxyl group of alkyl vanillates, neither these compounds nor alkyl vanillate - EBA compositions, particularly HV-EBA cements, inhibit polymerization of acrylic resins or composites. On the other hand, the inhibiting action of the commonly used materials, eugenol, or 2,5-dimethoxyphenol, when added in small amounts to the catalyst paste of a commercial composite demonstrates inhibition of polymerization as shown by the data in Table 3. Thus, the presence of even 0.1% of these compounds in the composite mix yields a soft polymer even after allowing 15 minutes to cure. Addition of 1% or 5% of these phenolic compounds further retards the polymerization. In comparison, neither EBA or HV in up to 5% concentration appreciably affect the polymerization.

TABLE 3

Inhibiting Effect of Phenolic Derivatives on the Cure of a bis-GMA type Commercial Composite

| Liquid added to Composite, %* | Cure Time in Minutes of Composite Containing | | | |
| | Eugenol | o-Ethoxybenzoic Acid | 2,5-Dimethoxyphenol | n-Hexyl Vanillate |
|---|---|---|---|---|
| 0 | 4–4.5 | 4–4.5 | 4–4.5 | 4–4.5 |
| 0.1 | ~30 (soft) | 4–4.5 | ~15 (soft) | 4–4.5 |
| 1 | >180 | 4 | ~90 (soft) | 4.5–5 |
| 5 | >1400 | 4–4.5 | >1400 | 6 |

*Phenolic derivatives were mixed into the catalyst paste.
Concentration based on total weight of pastes used to prepare composite (Adaptic Johnson and Johnson).

Not only is the rate of polymerization of resin that is contacted unchanged when using the newly developed cement, but also the surface properties of composites cured against the newly hardened cement remain unaltered. Table 4 gives the results of superficial indentation and recovery tests of the surface of a composite cured against HV-EBA cement which had been mixed 10 minutes before placement of the composite. The superficial hardness of composite specimens cured against the HV-EBA cements (57.6 $\mu$m) is similar to that of composite specimens (blanks) which were not in contact with cement. However, composites cured against ZOE cement had higher indentation (63.1 μm) and lower percent recovery values indicating an inhibited (lower degree) cure or polymerization resulting from the presence of eugenol at the resin-cement interface.

TABLE 4

Indentation and Percent Recovery of Composites Cured in Contact with Dental Cements Cement was cured for 10 min. prior to placing the composite.
Composite was stored in 100% RH for 24 hrs.

| Composite Cured Against | Indentation, mm[a] μm | Recovery, %[b] |
|---|---|---|
| Glass | 56.9 ± 3.5 | 76.3 ± 4.5 |
| ZOE Cement | 63.3 ± 3.1 | 70.3 ± 3.9 |
| HV-EBA | 57.6 ± 2.1 | 78.1 ± 2.8 |

[a] Using a 12.7 mm steel ball loaded at 30 kg for 10 min.
[b] 10 min. after release of the 30 kg load The HV-EBA cements adhere strongly to non-precious dental alloys and to amalgams, dental resins and composites. Tests have also shown that non-precious alloys or amalgams, disks or rods, when cemented together with the cements and placed in water also adhere strongly. Even after 12 months storage of the specimens in water, this bonding was still extremely strong. Similarly, cement disks cured against dental composite have demonstrated strong adhesion to the composite after 12 months storage in water. Cements based on ZOE or EBA do not bond to such substrates to any appreciable extent. A weaker bond is formed between the HV-EBA cement and gold, however.

The complete absence of inhibition of ZnO-alkyl vanillate cements, coupled with their excellent adhesion to resins and metals and their substantial compressive and tensile strength renders these materials highly desirable in applications for which ZOE cements are unsuitable. Thus, acrylic resins of composites may be placed over bases formed from the instant cement. A portion of the cement, when used clinically as a temporary restoration, or filling, may be retained as a base for an acrylic resin restoration. This avoids the procedure of completely reexposing deep cavities, thus further reducing irritation of the dental tissues.

Since the cementitious compositions of the present invention adhere extremely well to many polymeric materials, temporary restorations which incorporate polymers as reinforcing materials in the cements themselves were prepared and shown to be effective for such purposes. The polymers may be added to either the liquid or the powder, depending upon the solubility of the polymeric material in the liquid phase. Rubbery polymers, for instance, may be dissolved in the liquid; whereas solid polymers of small particle sizes (i.e. sizes comparable to those of the ZnO and $Al_2O_3$) may be incorporated in the powder.

A variety of polymeric materials may be used including poly-acrylates and methacrylates (derived from the corresponding monomers of the free acids and their alkyl esters); vinyl polymers including poly(vinyl acrylates) and methacrylates; poly(vinyl chloride); poly(vinyl acetate); polystyrene; polyacetal; polyurethanes; polycarbonates and various copolymers such as butadiene-acrylonitrile copolymers; acrylonitrile-butadiene-styrene terpolymers and vinyl chloride-vinyl acetate copolymers, as well as mixtures of the foregoing. Where high stress-bearing cements are sought, the poly(alkyl acrylates) and poly(alkyl methacrylates) are preferred, poly(methyl methacrylate) being most preferred. The polymeric material may be incorporated into the cement in amounts between 1 and 20% by weight of the total composition and preferably between 2 and 10%. Table 5 shows the results obtained by incorporating various polymeric materials in a preferred embodiment of the present invention.

TABLE 5

Composition - Powder: 64% ZnO; 30% $Al_2O_3$; 6% Hydrogenated rosin
Liquid: 12.5% Hexyl Vanillate; 87.5% EBA plus polymer additive dissolved in liquid.
Powder/Liquid Ratio: 1.3 g/0.2 ml liquid.

| Polymer Additive | Setting Time min. | Strength, Compressive | MPa Tensile |
|---|---|---|---|
| None | 5.5 | 61 | 5.0 |
| 2% Polyurethane (Estane 5712, B. F. Goodrich) | 5.0 | 65 | 5.7 |
| 3% Butadiene-acrylonitrile, vinyl terminated (Hycar 1300 X-22, B. F. Goodrich) | 6.0–6.5 | 61 | 5.7 |
| 10% Methacrylate copolymer (Acryloid K 120N, Rohm and Haas)[a] | 4.0 | 31 | 6.6 |
| 10% Vinylite VYHH[b] (Union Carbide)[a] | 6.0–6.5 | 76 | 8.2 |

[a] Added to the polymer powder
[b] vinylchloride-vinylacetate copolymer

With different powder to liquid (P/L) ratios, compositions having varying physical properties, useful for different dental applications, can be prepared (Table 6). Depending on the consistency, mixing characteristics and film thickness desired for specific applications, the materials are useful as intermediate restoratives, insulating bases, root canal restorations and as pulp capping and luting agents.

TABLE 6

Properties of n-Hexyl Vanillate-EBA Cements of Varying Powder-Liquid Ratios

Powder: 64% ZnO - 30% $Al_2O_3$ - 6% Hydrogenated Rosin
Liquid: 12.5% Hexyl Vanillate - 87.5% EBA

| Powder/ 0.2 ml liquid[d] (g) | Setting Time (min.) | Strength Compressive (MPa) | Tensile (MPa) | Water Solubility Wt. Loss of Disk (%) | $H_2O$ Residue (%) | Consistency (min) | Film Thickness (μm) |
|---|---|---|---|---|---|---|---|
| 2.0 | 6.0 | 88.2 ± 2.7 | 7.3 ± 0.4 | 0.28 | 0.01 | | — |
| 2.0[a] | — | 91.3 ± 8.2 | 7.8 ± 0.9 | 0.46 | 0.02 | 13.5 (120 g)[b] | |
| 1.7 | 6.5 | 83.6 ± 11.0 | 6.2 ± 0.8 | 0.24 | 0.02 | 21 (2500 g) | 184 |
| 1.3 | 5.5 | 61.4 ± 11.2 | 5.0 ± 0.1 | 0.51 | 0.10 | 31 (2500 g) | — |

TABLE 6-continued

Properties of n-Hexyl Vanillate-EBA Cements of Varying Powder-Liquid Ratios

Powder: 64% ZnO - 30% Al$_2$O$_3$ - 6% Hydrogenated Rosin
Liquid: 12.5% Hexyl Vanillate - 87.5% EBA

| Powder/ 0.2 ml liquid[d] (g) | Setting Time (min.) | Strength Compressive (MPa) | Strength Tensile (MPa) | Water Solubility Wt. Loss of Disk (%) | Water Solubility H$_2$O Residue (%) | Consistency (min) | Film Thickness (μm) |
|---|---|---|---|---|---|---|---|
| 1.1 | 6.0 | 68.6 ± 7.6 | 5.9 ± 0.5 | 0.58[c] | 0.12[c] | 35 (120 g) | 26.6 |

[a]Liquid: 62.5% EBA - 37.5 eugenol
[b]Load applied
[c]Water solubility of a commercial ZOE luting agent: Wt. loss of disk 3.16%; water residue: 0.02%
[d]American National Standards Institute - American Dental Association Specification No 30 was followed where applicable.

Generally, the larger the amount of powder incorporated per unit volume of liquid the greater is the strength and the lower the water solubility (Table 6). Too high a P/L ratio yields mixes of high consistency, which, because of poor handling characteristics, would not be suitable for clinical applications. Inclusive of all possible applications, the preferred range is 0.9-2.9 g powder/0.2 ml liquid, preferably 1.0-2.4 g of powder/0.2 ml.

The powder-liquid ratio to be employed depends on the ultimate use of the cement. Thus, a material prepared by mixing 1.1 g to 1.3 g of powder with 0.2 ml liquid is suitable as a luting agent for cementation of crowns and bridges where a material having a thin film thickness is preferred. Mixes of heavier consistency (see Table 6) are useful as insulating bases, and with or without modifications, as materials for temporary fillings. Other uses of these materials are as pulp capping agents, root canal restorations and, with modifications, as impression pastes. The material properties clearly surpass the requirements of American Dental Association Specification No. 30 for Dental Zinc Oxide-Eugenol Type Restorative Materials, Type III, Class 1 (filling materials and bases), and Type IV (cavity liners). If the powder components are sieved to give a proper film thickness in the hardened cement, these materials will significantly exceed the requirements of Type II, Class 1 cements (for permanent cementing purposes).

Comparison of data given in Table 6 shows that hexyl vanillate HV-EBA disks solubilize considerably less than disks prepared from EBA-eugenol cements employing the same P/L ratio of 2.0 g/0.2 ml. Similarly, at a luting consistency, HV-EBA disks lose much less weight than those prepared from a commercial ZOE cement.

Specimens with the composition given in Table 7 were prepared according to the ADA Specification No. 30, immersed in water that was changed weekly and weighed after various time periods. The table compares solubility data for the cement specimens containing hexyl vanillate-EBA and those prepared from a commercial ZOE cement.

TABLE 7

Solubility and Disintegration of Hexyl Vanillate-EBA Cements (HV-EBA)

Powder: 64% ZnO; 30% Al$_2$O$_3$; 6% Hydrogenated Rosin
Liquid: 12.5% Hexyl Vanillate; 87.5% EBA
Powder/Liquid Ratio: 1.3 g/0.2 ml for the experimental cement;
0.67 g/0.2 ml for commercial material as recommended in the manufacturer's instructions Average Change in Weight (%)

TABLE 7-continued

Solubility and Disintegration of Hexyl Vanillate-EBA Cements (HV-EBA)

| Material | 1 day | 1 month | 6 months[a] |
|---|---|---|---|
| HV-EBA | −0.27 | 0.48 | 0.80 |
| ZOE[b] | −1.85 | −3.38 | −12.40 |

[a]When the water in which the specimens were stored during the last week prior to the 6 month storage period was evaporated the weight of the solid residue was, respectively, 0.5% for the HV-EBA specimens and 0.8% for the ZOE material.
[b]Commonly used commercial ZOE cement.

The superior physical and chemical properties described above may be obtained by another variant of the present invention, a vanillate cross-linking agent. In the case of the alkyl vanillates or most chelating compounds, it is generally accepted that a single divalent metal ion is capable of complexing two molecules of chelating compound as an independent unit. However, when the organic molecule contains two or more vanillate groups an extended network can occur since each organic molecule contains two or more "chelating" sites capable of reacting with a metal ion. Such di- or polyvanillates which are suitable for use in the present invention may be prepared by reaction of vanillic acid or its isomers with a suitable polyhydric compound such as a glycol or polyol, according to a standard esterification reaction as that outlined above and set forth in detail in the examples below. As in the case of the monovanillates, the suitability of the polyhydric compound is determined by its overall effect on the physical state of the resultant polyvanillate, a liquid at temperatures of about 55° C. or below being the prime requirement. Thus, for preparing di- and polyvanillate esters, branched, straight chain and cyclic polyols and α, ω-glycols may be used, having from about 4 to 15 carbon atoms, with those having 5 to 12 carbon atoms preferred. The di- and polyvanillate esters may be used in addition to or substituted in whole or in part for monoalkyl esters described heretofore. Low melting solid and liquid polyalkylene glycols may also be used as for example polyethylene glycols such as the Carbowaxes or PEG with molecular weights below approximately 2000.

In view of the absence of any inhibitory effect on free radical polymerization and the strong adhesion of the cementitious compositions described above, other compositions may be formulated which additionally contain a polymerizable monomer, a polymerization initiator and a polymerization accelerator. These monomer containing compositions, because of their superior mechanical properties, particularly their compressive and tensile strengths, may be employed as permanent restoratives.

Suitable monomers include those which polymerize by a free radical mechanism, preferred being those containing one or more acrylate, methacrylate or vinyl groups. Particularly preferred are those compounds which cure by a redox initiator-accelerator mechanism or by irradiation. Examples of such preferred compounds include alkyl acrylates and methacrylates, such as methyl and ethyl acrylate and methacrylate, alkylene glycol diacrylates and dimethacrylates in which the alkylene group contains 2 to 12 carbon atoms and polyol polyacrylates and polymethacrylates in which the polyol contains 2 to 12 carbon atoms and the number of acrylate or methacrylate moieties per polyol radical is between 2 to 6. The monomer is mixed with the liquid in the range of 2.5 to 75% by weight, based on the weight of the liquid phase, preferably 5 to 60%.

Any compound capable of initiating polymerization of such monomers is suitable, particularly peroxides, such as benzoyl or lauryl peroxide, or the methyl ether of benzoin. The initiator is used in concentrations of approximately 0.5 to 2% by weight, based on the weight of the liquid phase.

Compounds which are conventionally used to accelerate such polymerization reactions may be employed in this embodiment. Amines, particularly tertiary amines, are quite suitable if diacyl peroxide is the initiator, and a discussion of those which may be used in this type of reaction are described by Brauer et al., in "4-N,N-Dialkylaminophenethanols, Alkanoic Acids and Esters: New Accelerators for Dental Composites", JOURNAL OF DENTAL RESEARCH, Volume 60, pp. 1343-1348, July 1981. The preferred compounds include p-(dimethylamino)phenethanol and p-(diethylamino)phenylacetic acid. Based on the weight of the liquid phase, the accelerator should be present in concentrations of approximately 0.05 to 0.11%, by weight.

If free radical polymerizable monomers are present, to extend storage stability, a trace amount of an inhibitor may be added to the liquid.

When compositions containing monomers are employed, reinforcing fillers may be added in amounts of up to 80% by weight of the solid phase to improve mechanical strength. Glass or silica of the type generally employed in the formulation of conventional dental composite resins are acceptable. Preferably, the fillers are silanized and coated with initiator by conventional techniques.

The following examples provide details of the manner and mode of making and using various embodiments of the present invention. Neither these examples nor any of the foregoing disclosure should be construed as limiting in any way of the scope of the present invention.

VANILLATE ESTERS

Example 1

Hexyl vanillate was synthesized according to the method of Pearl, I.A., and McCoy, J. F. "Reaction of Vanillin and its Derived Compounds. Some Esters of Vanillic Acid." J. AM. CHEM. SOC. 69: 3071 (1947). Vanillic acid (20.2 g, 0.12 mol) was refluxed with n-hexanol (29.9 ml, 0.24 mol) in the presence of p-toluenesulfonic acid (0.2 g) for 26 hours. After the unreacted alcohol was removed by distillation in a vacuum, the hexyl vanillate was distilled and obtained in 86% yield.

Example 2

Heptyl vanillate was synthesized by a procedure similar to that described for the hexyl compound and has a boiling point of 181°-183° C. at 2 mm pressure and a melting point at 29.5° C. to 30° C. (Yield: 70%).

Example 3

The n-decyl vanillate was synthesized by refluxing decyl alcohol with vanillic acid in the presence of p-toluenesulfonic acid. After removal of the unreacted alcohol, purification and recrystallization from n-pentane, the n-decyl vanillate had a melting point of 40°-40.5° C. (Yield: about 50%).

Example 4

2-Ethylhexyl vanillate was prepared from the corresponding, dry alcohol (13.0 g, 0.10 mol) vanillic acid (8.4 g, 0.05 mol) and 0.1 g p-toluenesulfonic acid. After refluxing for 27 hours and extraction with aq. $NaHCO_3$ solution and $H_2O$ the product distilled at 192°-193° C. at 2 mm. The slightly yellow viscous liquid was 98-98.5% pure (as determined by gas chromatography). (Yield: 91%)

Example 5 n-Hexyl isovanillate was obtained on refluxing n-hexanol (dried over molecular sieve), 10.2 g (0.1 mol), isovanillic acid (3-hydroxy-4-methoxybenzoic acid, 8.4 g, 0.05 mol), 0.1 g p-toluenesulfonic acid and 100 ml toluene for 24 hr. Most of the solvent was distilled off, another 0.1 mol alcohol and xylene were added, and the mixture was refluxed an additional 10 hours. The unreacted acid was filtered off. After addition of methylene chloride, and extraction with aq. $NaHCO_3$ solution, the organic layer was dried and distilled. The n-hexyl isovanillate distilled at 173° C./2.5 mm. The slightly viscous, yellow liquid proved 97-98% pure (gas chromatographic anlysis). (Yield: 59%).

Example 6

The diester, 1,10-decamethylene divanillate, was prepared by combining 1,10-decanediol (0.025 mol) and vanillic acid (0.063 mol) in the presence of 0.25 g p-toluenesulfonic acid. The mixture, dissolved in 50 ml toluene and 40 ml tetrahydrofuran, was refluxed for 30 hrs and stripped of solvent. The residue was purified by extraction with mild base. The dark brown oil was dissolved in methanol and boiled with activated carbon to remove impurities. The diester was characterized by infrared and GLC analyses and appeared to be 95% pure.

Example 7

Polymeg 2000 (Quaker Oats Co.), a polyalkylene, oligomeric diol was esterified with vanillic acid according to the reaction.

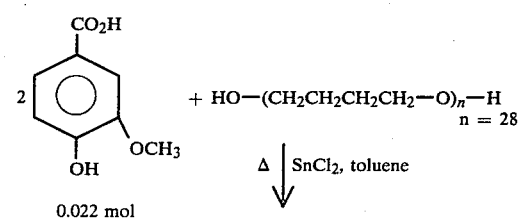

-continued

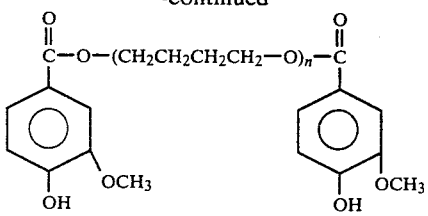

The product obtained by this reaction was a waxy solid. m.p.=28° C., yield 65%, and was characterized by IR analysis.

DENTAL CEMENT COMPOSITIONS

Example 8

64 g reagent grade zinc oxide (such as Mallinckrodt Co., Reagent grade) was sieved through a No. 70 or smaller opening size sieve. The powder was placed in a V-shaped blender with 30 g aluminum oxide (pretreated by heating for 4 or 5 hours to 700° C., cooling and sieving through a No. 270 mesh sieve) and 6 g hydrogenated rosin (Staybelite resin, Hercules, Inc., passed through a No. 100 sieve). The powder is mixed end-over-end for 24 hours. The liquid is prepared by thoroughly dissolving 5.0 g hexyl vanillate in 35 g of o-ethoxybenzoic acid (EBA). A 1.7 g portion of the powder was mixed with 0.2 ml of the liquid using a spatula on a glass slab. The mixture hardened in 6.5 min, at 37° C. in a 100% relative humidity environment using the setting time test employed in ADA Specification No. 30 for Dental Zinc Oxide-Eugenol Type Restorative Materials.

Example 9

1.3 g of powder of the same composition as given in Example 8 was mixed with 0.2 ml liquid containing 13.2% heptyl vanillate-86.8% EBA. The material hardened in 5.5 to 6.0 min., yielding a cement with a compressive strength of 58.3 MPa and a tensile strength of 6.3 MPa.

Example 10

1.3 g of powder of the composition given in Example 8 was mixed with 0.2 ml of liquid (15.3% n-decyl vanillate dissolved in 84.7% EBA; that is, a formulation containing a mole percent concentration of n-decyl vanillate equal to that of hexyl vanillate given in Example 8). The material hardened in 4.5 min and had a compressive strength of 50.1 MPa and tensile strength of 5.6 MPa.

Example 11

1.3 g of powder of the composition given in Example 8 was mixed with 0.2 ml of liquid containing 13.9% 2-ethylhexyl vanillate and 86.1% EBA (equal to mole percentage given in Example 8). The material hardened in 5.5 min and had a compressive strength of 48.5 MPa.

Example 12

Isomers and homologs of vanillic acid, or their esters, that are capable of forming chelates when dissolved in EBA and mixed with zinc oxide also form cementitious materials with desirable properties.

1.3 g of powder of the composition given in Example 1 is mixed with 0.2 ml of liquid containing 10.4% ethyl homovanillate (commercial) and 89.6% EBA (equal to the molar composition of the liquid in Example 1). The mix hardens in 5 min and has a compressive strength of 54.1±4.7 MPa.

Example 13

1.3 g of powder of the composition given in Example 8 was mixed with 0.2 ml of liquid containing 11% 1,10-decamethylene divanillate and 89% EBA (equal to the molar composition of the liquid used in Example 8). The mix hardened in 4.5 min to give a cement with compressive strength of 70.6 MPa and a tensile strength of 7.5 MPa.

Example 14

The diester, 1,6-hexamethylene divanillate prepared in the same manner as the 1,10-decamethylene divanillate, was incorporated into the same liquid described in Example 8, 10.3% by weight. This was then mixed with the powder of Example 8. The resulting mix hardened in 5 min and had a compressive strength of 47.8±3.8 MPa and tensile strength of 6.2±0.8 MPa.

Example 15

The powder of the composition given in Example 8 was thoroughly mixed with 0.1% finely powdered benzoyl peroxide.

To the liquid containing 12.5% hexyl vanillate-87.5% EBA was added 10% of 1,10-decamethylene glycol dimethacrylate containing 0.5% p-(dimethylamino)phenethanol accelerator.

The powder and liquid were mixed employing 1.3 g of powder per 0.2 ml liquid. The material hardened in 6 min. The cement had a compressive strength of 79.4±1.8 MPa and a tensile strength of 6.3±0.8 MPa.

Example 16

A powder was prepared from 64% zinc oxide, 30% aluminum oxide and 6% hydrogenated rosin. Two parts of this powder were mixed with 1 part glass (Corning Glass 7724) silanized with 3-methacryloxypropyltrimethoxysilane which had been coated with 1% benzoyl peroxide. The liquid consisted of a mixture of 1 part of 12.5% hexyl vanillate-87.5% EBA and 1 part 1,10-decamethylene glycol dimethacrylate containing 0.5% p-(dimethylamino)phenylacetic acid.

The powder and liquid were mixed in a ratio of 1.8 g powder per 0.2 ml liquid. The material hardened in 6 minutes. The hardened cement had a compressive strength of 137.6±5.8 MPa, and a tensile strength of 14.1 MPa.

We claim:

1. A cementitious dental composition comprising a solid phase which includes a metal oxide or hydroxide of tin or a Group II metal and a liquid phase which includes a chelating compound, said chelating compound comprising an ester of a vanillic acid moiety, said ester being the product of a reaction of an alcohol and at least one of a member selected from the group consisting of vanillic acid, isomers of vanillic acid, and homologs of vanillic acid.

2. The cementitious dental composition of claim 1, wherein said alcohol is straight or branched chain alcohols having from 4 to 15 carbon atoms.

3. The cementitious dental composition of claim 2, wherein said alcohol is n-hexyl alcohol.

4. The cementitious dental composition of claim 1, wherein said vanillic acid moiety is vanillic acid.

5. The cementitious dental composition of claim 1, wherein said vanillic acid moiety is 3-hydroxy-4-methoxybenzoic acid.

6. The cementitious dental composition of claim 1, wherein said vanillic acid moiety is homovanillic acid.

7. The cementitious dental composition of claim 1, wherein said ester is n-hexyl vanillate.

8. The cementitious dental composition of claim 1, wherein said metal oxide is zinc oxide.

9. The cementitious dental composition of claim 1, wherein said solid phase additionally contains an hydrogenated resin.

10. The cementitious dental composition of claim 1, wherein said solid phase additionally contains $Al_2O_3$.

11. The cementitious dental composition of claim 1, wherein said ester is liquid at a temperature of 55° C.

12. The cementitious dental composition of claim 1, wherein said liquid phase additionally contains a second chelating compound.

13. The cementitious dental composition of claim 12, wherein said second chelating compound is a member selected from the group consisting of o-ethoxybenzoic acid, o-salicylaldehyde, o-ethoxybenzoyl chloride, 2-methoxy-4-phenylphenol, 2-propoxy-5-methylbenzoic acid, lactic acid, ethoxyacetic acid, acetylacetone, ethyl acetoacetate, citraconic anhydride and ethylenediamine.

14. The cementitious dental composition of claim 12, wherein said second chelating compound is o-ethoxybenzoic acid.

15. The cementitious dental composition of claim 1, wherein said composition additionally contains an acid.

16. The cementitious dental composition of claim 15, wherein said acid is a carboxylic acid.

17. The cementitious dental composition of claim 16, wherein said carboxylic acid is present in an amount of between 0.1 to 10% by weight, based on the weight of the composition.

18. The cementitious dental composition of claim 16, wherein said carboxylic acid is acetic acid, acrylic acid, methacrylic acid, polyacrylic acid, hydrocinnamic acid, polycarboxylated styrene or dimethylolpropionic acid.

19. The cementitious dental composition of claim 1, wherein said ester is a divanillate ester which is the product of the reaction of said vanillic acid moiety and a polyhydric alcohol.

20. The cementitious dental composition of claim 19, wherein said polyhydric alcohol is 1,6-hexamethylenediol.

21. The cementitious dental composition of claim 19, wherein said polyhydric alcohol is 1,10-decamethylenediol.

22. The cementitious dental composition of claim 1, wherein the weight of said solid phase per 0.2 ml of liquid phase is in the range of 0.9 to 2.9 grams.

23. The cementitious dental composition of claim 22, wherein the weight of solid phase per 0.2 ml of liquid phase is in the range of 1.0 to 2.4 grams.

24. The cementitious dental composition of claim 12, wherein said liquid phase comprises by weight, based on the weight of said liquid phase, between 2.5 to 35% of said ester and between 65 to 97.5% of said second chelating compound.

25. The cementitious dental composition of claim 12, wherein said liquid phase comprises by weight based on the weight of said liquid phase between 5 to 25% of said ester and 75 to 95% of said second chelating compound.

26. The cementitious dental composition of claim 12, wherein said phase comprises by weight, based on the weight of liquid phase, 12.5% n-hexyl vanillate and 87.5% o-ethoxybenzoic acid.

27. The cementitious dental compression of claim 1, wherein said solid phase comprises by weight, 40 to 98% ZnO, 2 to 15% hydrogenated rosin and 0 to 50% $Al_2O_3$.

28. The cementitious dental composition of claim 1, comprising by weight, a solid phase comprising 64% ZnO, 30% $Al_2O_3$ and 6% hydrogenated rosin and liquid phase comprising 12.5% n-hexyl vanillate and 87.5% o-ethoxybenzoic acid.

29. The cementitious dental composition of claim 1, wherein said composition additionally contains a polymeric material.

30. The cementitious dental composition of claim 29, wherein said polymeric material is selected from the group consisting of poly(alkyl acrylates), poly(alkyl methacrylates), poly(vinyl chloride), poly(vinyl acetate), polystyrene, polyacetal, polyurethanes, polycarbonates, butadiene-acrylonitrile copolymers, vinyl chloride-vinyl acetate copolymers, acrylonitrile-butadiene-styrene terpolymers and mixtures of the foregoing.

31. The cementitious dental composition of claim 29, wherein said polymer is present in said composition in an amount of between 1 to 20% by weight, based on the weight of said composition.

32. The cementitious dental composition of claim 31, wherein said polymer is present in said composition in an amount of between 2 to 10% by weight, based on the weight of said composition.

33. The cementitious dental composition of claim 1, wherein said composition additionally contains a polymerizable monomer.

34. The cementitious dental composition of claim 33, wherein said polymerizable monomer polymerizes by a free radical mechanism and said composition further contains a polymerization initiator and a polymerization accelerator.

35. The cementitious dental composition of claim 34, wherein said polymerizable monomer cures by a redox-initiator-accelerator mechanism or by irradiation.

36. The cementitious dental composition of claim 33, wherein said polymerizable monomer contains at least one acrylate, methacrylate or vinyl group.

37. The cementitious dental composition of claim 33, wherein said polymerizable monomers is selected from the group consisting of alkyl acrylates, alkyl methacrylates, alkylene diacrylates, alkylene dimethacrylates, polyol polyacrylates and polyol polymethacrylates.

38. The cementitious dental composition of claim 37, wherein said alkyl group is methyl or ethyl.

39. The cementitious dental composition of claim 37, wherein said alkylene group contains 2 to 12 carbon atoms.

40. The cementitious dental composition of claim 37, wherein said polyol radical contains 2 to 12 carbon atoms and the number of acrylate or methacrylate moieties in said polyol polyacrylates and polyol polymethacrylates, respectively, per polyol radical, is between 2 to 6.

41. The cementitious dental composition of claim 33, wherein said monomer is present in an amount of between 2.5 to 75% by weight, based on the weight of the liquid phase.

42. The cementitious dental composition of claim 33, wherein said monomer is present in an amount of between 5 to 60% by weight, based on the weight of the liquid phase.

43. The cementitous dental composition of claim 28, wherein said composition further contains a polymeric material selected from the group consisting essentially of poly(alkyl acrylates), poly(alkyl methacrylates), poly(vinyl acrylates), poly(vinyl methacrylates), poly(vinyl chloride), poly(vinyl acetate), polystyrene, polyacetal, polyurethanes, polycarbonates, butadiene-acrylonitrile copolymers, vinyl chloride-vinyl acetate copolymers, acrylontrile-butadiene-styrene terpolymers and mixtures of the foregoing in an amount of between 2 to 10% by weight, based on the weight of said composition.

44. The cementitious dental composition of claim 28, wherein said composition additionally contains a polymerizable monomer selected from the group consisting of methyl acrylate, methyl methacrylate, ethyl acrylate and ethyl methacrylate, in an amount of between 5 to 60% by weight based on the weight of the liquid phase; a polymerization initiator and a polymerization accelerator.

45. The cementitious dental composition of claim 28, wherein said composition additionally contains a polymerizable monomer selected from the group consisting of polyol polyacrylates and polyol polymethacrylates, in an amount of between 5 to 60% by weight, based on the weight of the liquid phase; a polymerization initiator; and a polymerization accelerator, with the proviso that said polyol radical contain between 2 and 12 carbon atoms and the further proviso that in said polyol polyacrylates and polyol polymethacrylates the number of acrylate or methacrylate moieties, respectively, is between 2 and 6.

46. The cementitious dental composition of claim 28, wherein said composition additionally contains a polymerizable monomer selected from the group consisting of alkylene diacrylates and alkylene dimethacrylates, in an amount of between 5 to 60% by weight, based on the weight of the liquid phase; a polymerization initiator and a polymerization accelerator, with the proviso that said alkylene group contain 2 to 12 carbon atoms.

* * * * *